(12) United States Patent
Harris et al.

(10) Patent No.: US 8,639,350 B2
(45) Date of Patent: Jan. 28, 2014

(54) TELEMETRY DOUBLE BUFFERING AND OVERSAMPLING FOR AN IMPLANTABLE MEDICAL DEVICE

(71) Applicant: Cardiac Pacemakers, Inc., St. Paul, MN (US)

(72) Inventors: Thomas J. Harris, Shoreview, MN (US); Ron A. Balczewski, Bloomington, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/845,344

(22) Filed: Mar. 18, 2013

(65) Prior Publication Data

US 2013/0222152 A1 Aug. 29, 2013

Related U.S. Application Data

(62) Division of application No. 12/325,966, filed on Dec. 1, 2008, now Pat. No. 8,406,891.

(60) Provisional application No. 61/007,457, filed on Dec. 12, 2007.

(51) Int. Cl.
*A61N 1/00* (2006.01)
*A61B 19/00* (2006.01)

(52) U.S. Cl.
USPC .............. 607/60; 607/30; 607/31; 128/903; 128/904

(58) Field of Classification Search
USPC .................. 607/30–31, 60; 128/903–904
See application file for complete search history.

(56) References Cited

U.S. PATENT DOCUMENTS

| | | | |
|---|---|---|---|
| 4,008,378 | A | 2/1977 | Nance et al. |
| 5,487,754 | A | 1/1996 | Snell et al. |
| 6,738,670 | B1 | 5/2004 | Almendinger et al. |
| 7,060,030 | B2 | 6/2006 | Von Arx et al. |
| 7,127,297 | B2 | 10/2006 | Law et al. |
| 7,254,448 | B2 | 8/2007 | Almendinger et al. |
| 8,406,891 | B2 | 3/2013 | Harris et al. |
| 2009/0216297 | A1 | 8/2009 | Harris et al. |

OTHER PUBLICATIONS

"U.S. Appl. No. 12/325,966, Final Office Action mailed Jun. 10, 2011", 12 pgs.
"U.S. Appl. No. 12/325,966, Non Final Office Action mailed Feb. 18, 2011", 11 pgs.
"U.S. Appl. No. 12/325,966, Notice of Allowance mailed Nov. 29, 2012", 8 pgs.
"U.S. Appl. No. 12/325,966, Response filed May 9, 2011 to Non-Final Office Action mailed Feb. 18, 2011", 12 pgs.
"U.S. Appl. No. 12/325,966, Response filed Aug. 29, 2011 to Final Office Action mailed Jun. 10, 2011", 11 pgs.
"U.S. Appl. No. 12/325,966, Response filed Dec. 1, 2010 to Restriction Requirement mailed Nov. 15, 2010", 8 pgs.
"U.S. Appl. No. 12/325,966, Restriction Requirement mailed Nov. 15, 2010", 5 pgs.

*Primary Examiner* — Nicole F Lavert
(74) *Attorney, Agent, or Firm* — Schwegman Lundberg & Woessner, P.A.

(57) ABSTRACT

A method of operating an implantable medical device (IMD) includes demodulating a data signal incoming to the IMD, serially storing demodulated data received in the data signal in a first serial buffer register, transferring the received demodulated data to a parallel buffer register from the first serial buffer register, wherein the parallel buffer register operates according to a clock signal having a lower frequency than a clock signal used to operate a serial buffer register, switching the serial storing of demodulated data to a second serial buffer register during the transferring of the received demodulated data to the parallel buffer register, and alternating the serial storing of the received data between the first and second serial buffer registers.

20 Claims, 2 Drawing Sheets

United States Patent US 8,639,350 B2

TELEMETRY DOUBLE BUFFERING AND OVERSAMPLING FOR AN IMPLANTABLE MEDICAL DEVICE

CLAIM OF PRIORITY

This application is a divisional of U.S. patent application Ser. No. 12/325,966, which is now U.S. Pat. No. 8,406,891, issued on Mar. 26, 2013, which further claims priority under 35 U.S.C. §119(e) to U.S. Patent Application Ser. No. 61/007,457, filed Dec. 12, 2007, each of which is incorporated herein by reference in its entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of two or more such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability. It is desirable to a physician to tailor a device to a specific patient's condition.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

Figure 1:
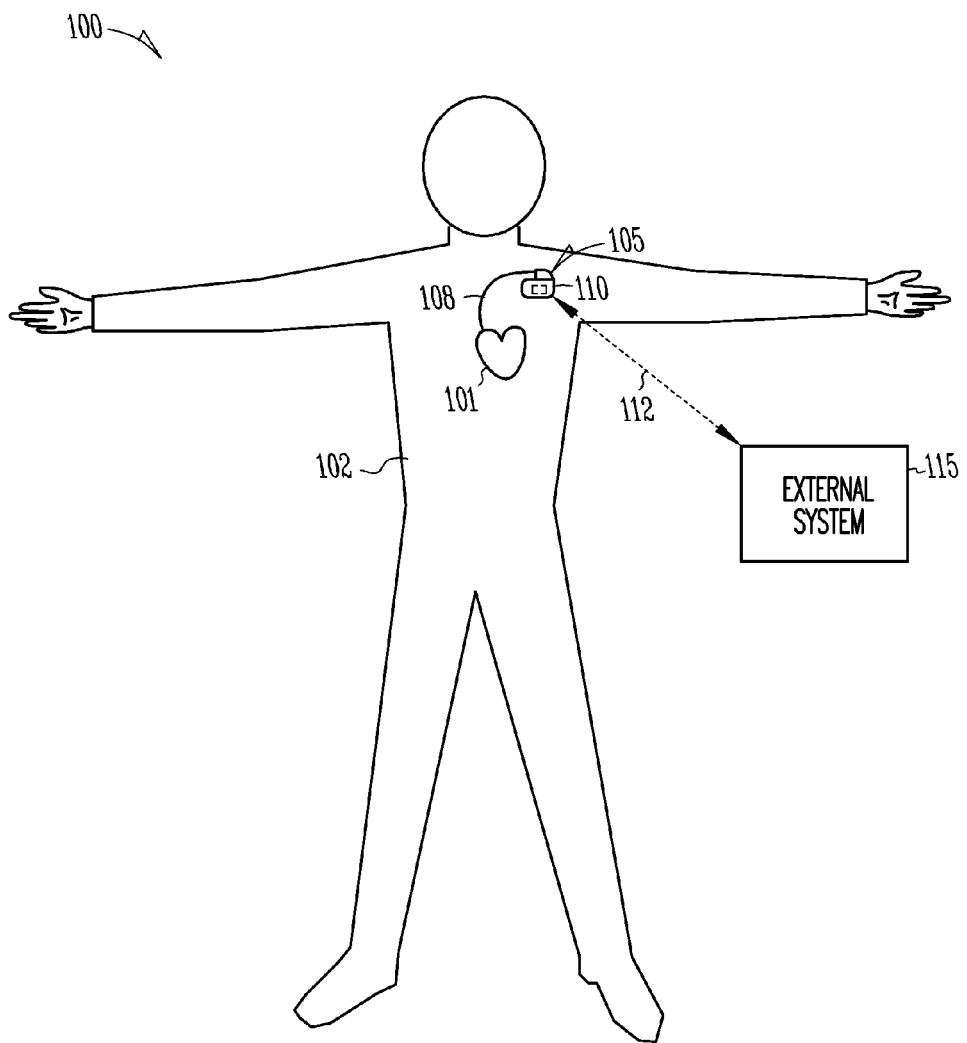
FIG. 1 is an illustration of an example of a cardiac rhythm management (CRM) system.

FIG. 1 is an illustration of an example of a cardiac rhythm management (CRM) system 100 and portions of an environment in which system 100 is used. System 100 includes an implantable system 105, an external system 115, and a telemetry link 112 providing for communication between implantable system 105 and external system 115.

Implantable system 105 includes, among other things, implantable medical device 110 and lead system 108. In various examples, implantable medical device 110 is an implantable CRM device including one or more of a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 1, implantable medical device 110 is implanted in a body 102. In various examples, lead system 108 includes leads for sensing physiological signals and delivering pacing pulses, cardioversion/defibrillation shocks, neurostimulation, pharmaceutical agents, biological agents, and/or other types of energy or substance for treating cardiac disorders. In various examples, electrodes placed in a heart 101 or other portions of body 102 are used to sense physiological signals and deliver pacing pulses, cardioversion/defibrillation shocks, neurostimulation, pharmaceutical agents, biological agents, and/or other types of energy or substance for treating cardiac disorders. In an example, lead system 108 includes one or more pacing-sensing leads each including at least one electrode placed in or on heart 101 for sensing one or more electrograms and/or delivering pacing pulses. In a specific example, lead system 108 allows pacing pulses to be delivered to multiple atrial and ventricular sites.

Implantable medical device 110 includes a hermetically sealed "can" to house electronic circuitry that performs sensing and therapeutic functions. In an example, an intermittent pacing system is housed within the hermetically sealed can. In another example, an intermittent pacing system includes internal components housed within the hermetically sealed can and external components located external to the hermetically sealed can but communicatively coupled to the internal components.

External system 115 allows a user such as a physician or other caregiver or a patient to control the operation of implantable medical device 110 and obtain information acquired by implantable medical device 110. In an example, external system 115 includes a programmer communicating with implantable medical device 110 bi-directionally via telemetry link 112. In another example, external system 115 is a patient management system including an external device communicating with a remote device through a telecommunication network. The external device can be within the vicinity of implantable medical device 110 and can communicate with implantable medical device 110 bi-directionally via telemetry link 112. The remote device can be remote from one or both of the external device and the IMD and allows the user to monitor or treat a patient from a distant location.

Telemetry link 112 provides for data transmission from implantable medical device 110 to external system 115. This can include, for example, transmitting real-time physiological data acquired by implantable medical device 110, extracting physiological data acquired by and stored in implantable medical device 110, extracting therapy history data stored in implantable medical device 110, or extracting data indicating an operational status of implantable medical device 110 (e.g., battery status and lead impedance). Telemetry link 112 also provides for data transmission from external system 115 to implantable medical device 110. This can include, for example, programming implantable medical device 110 to acquire physiological data, programming implantable medical device 110 to perform at least one self-diagnostic test (such as for a device operational status), or programming implantable medical device 110 to deliver one or more therapies.

Double Buffer

Figure 2:
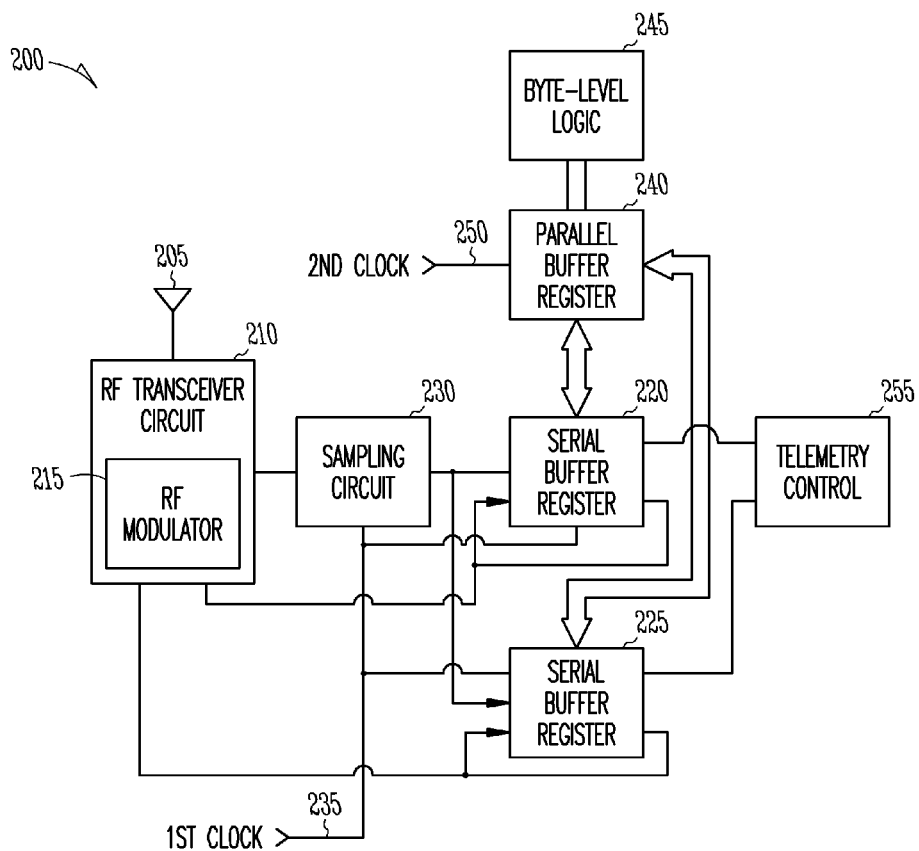
FIG. 2 is a block diagram of portions of an example of a communication circuit for an IMD.

FIG. 2 is a block diagram of portions of an example of a communication circuit 200 for an IMD. The communication circuit 200 includes a far-field antenna 205 and a radio frequency (RF) transceiver circuit 210. The far-field antenna 205 provides bidirectional RF wireless communication with an external system. RF transceiver circuit 210 includes an RF modulator 215 to modulate data signals outgoing from the IMD and to detect and demodulate data signals incoming to the IMD. The communication circuit 200 also includes a first serial buffer register 220 and a second serial buffer register 225. The first and second serial buffer registers 220, 225 serially receive demodulated data from the RF modulator 215.

Figure 3:
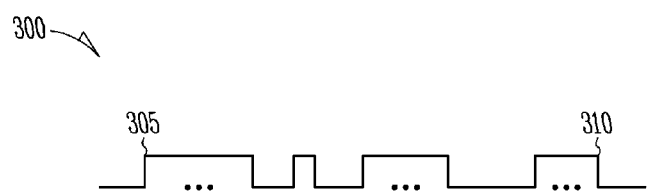
FIG. 3 is a conceptual illustration of a timing diagram of a data signal output from a radio frequency (RF) modulator.

FIG. 3 is a conceptual illustration of a timing diagram of a data signal 300 output from the RF modulator 215. The data signal 300 represents a demodulated data signal incoming to the IMD. To translate the data signal 300 into bits of data, the communication circuit 200 can include a sampling circuit 230. The sampling circuit 230 detects an edge transition 305 and, at a specified time from the edge based on the bit rate, samples the data signal 300 to determine binary "1"s and "0"s. In the illustration, the data signal 300 shown from edge transition 305 to edge transition 310 represents data string "111110010011110000111". The demodulated data is oversampled at a relatively high clock rate for an IMD so that data is not missed and to provide some noise immunity. In some examples, the sampling circuit samples at three specified times from the detected edge transition 305 to determine 1s and 0s. The data bit value can be determined using a majority of the three samples. This majority sampling provides improved noise immunity.

The sampling circuit 230 samples the data signal 300 according to a first clock signal 235. The serial buffer registers 220, 225 serially receive the demodulated data at the first clock signal 235. However, IMDs operate on a battery and therefore have a limited supply of energy. The first clock signal 235 may be a relatively a high clock rate for IMDs (e.g., 2 megahertz (MHz)) to provide the oversampling, and running the entire IMD at this clock rate may shorten the battery life of an IMD.

The communication circuit 200 also includes a parallel buffer register 240. The parallel buffer register 240 receives data in a parallel fashion from the serial buffer registers 220, 225. The parallel buffer register 240 provides the interface to byte level logic 245 of the IMD. The parallel buffer register 240 and the byte level logic 245 of the IMD can operate according to a second clock signal 250, which is slower than the first clock signal (e.g., 100 kilohertz (kHz) or 32 kHz). Running the byte level logic 245 at the slower second clock rate results in a lower amount of energy used by the IMD and extends the battery life of the IMD.

The communication circuit 200 also includes a telemetry control circuit 255. Because the demodulated data is being received at a high clock rate and the register serially receiving the data is being unloaded using a slow clock rate, double buffering can be provided, such as by using the first and second serial buffer registers 210, 215.

When the communication circuit 200 is in the receive mode, the telemetry control circuit 255 alternates the receiving of data between the first serial buffer register 220 and the second serial buffer register 225. For example, demodulated data is serially loaded into the first serial buffer register 200 until it reaches a number of bits (e.g., 8 or 10 bits). The telemetry control circuit 255 then disables the serial loading of data into the first serial buffer register 220, and enables the serial loading in the second serial buffer register 225. A specified time after serial loading has begun in the second serial buffer register 225 (e.g., a specified bit time), the data in the first serial buffer register 220 is loaded into the parallel buffer register 240.

Similarly, when the specified number of bits are loaded into the second serial buffer register 225, the telemetry control circuit 255 then disables serial loading into the second serial buffer register 225, and enables serial loading into the first serial buffer register 220. The data in the second serial buffer register 225 is then loaded into the parallel buffer register 240. Thus, the telemetry control circuit 255 alternates between serially receiving data into the first and second serial buffer registers 220, 225 and loading data into the parallel buffer 240 from the registers. The double buffering allows the data in a serial buffer register to be stable while it is unloaded without missing any new data from the RF modulator 215.

When the communication circuit 200 is in the transmit mode, the telemetry control circuit 255 alternates between sending data to the RF modulator 215 from a serial buffer register and loading a serial buffer register from the parallel buffer register 240. For example, data is loaded in a parallel fashion from the parallel buffer register 240 into the first serial buffer register 220. Data is then shifted out serially to the RF modulator 215 for modulation and transmission. At a specified time after the first serial buffer register 220 has begun shifting out data (e.g., a specified bit time), data is loaded in parallel from the parallel buffer register 240 to the second serial buffer register 225.

When all bits of the first serial buffer register 220 have shifted out, the telemetry control circuit 255 disables serial shifting of the first serial buffer register 200 and enables serial shifting of the second serial buffer register 225. A specified time after the second serial buffer register 225 has begun serially shifting data, data is loaded in parallel from the parallel buffer register 240 into the first serial buffer register 225. Thus, the telemetry control circuit 255 alternates between serially sending data to the RF modulator 215 from the first and second serial buffer registers 220, 225 and loading data into the registers from the parallel buffer 240. The double buffering allows the data in a serial buffer register to be stable while it is serially sent to the RF modulator 215.

Boundary Character

When transmitting or receiving data wirelessly between an external system and an implantable device, the DC component of the transmitted data signal can become imbalanced. This DC component can be conceptualized as the mean value of the signal waveform. If the DC component drifts toward one or the other of the voltage rails, the communication circuit 200 may become more susceptible to signal noise. To avoid DC imbalance, 8b/10b encoding of data can be used. In 8b/10b encoding, an 8 bit byte of data is translated to 10 bits. The extra two bits are chosen so that the difference between the number of "1s" and "0s" in a 20 bit string is never more than two, and so that there are no more than five "1s" or "0s" in a row. Avoiding communicating too many same-value bits in a row reduces the chances that DC imbalance will occur.

A challenge in communicating data between an IMD and an external system is indicating the word or frame boundaries in the communicated data. To indicate such a boundary, a value of "1100000101" can be used. This is a value that is never encountered in typical 8b/10b encoding algorithms. This value can be referred to as a "comma character" and can be sent to indicate a beginning of a communication session and to cause the telemetry control circuit 255 to enable portions of the communication circuit 200 or to wake-up other circuits in the IMD.

Transmitting the comma character is useful for other reasons. When a transition is detected, the initial two "1s" can be used to set attenuation thresholds for the receiving analog circuitry. For example, if the antenna of the external system is too close to the IMD, the first two "1s" and following five "0s" provide time to adjust the signal amplitude using an analog attenuator circuit. The trailing "101" can be used to detect a communication boundary. In this way, the comma character can be configured to serve the dual purpose of demarcation and signal level adjustment.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description, with each claim standing on its own as a separate example. The scope of the invention should be determined with reference to the appended claims, along with the full scope of equivalents to which such claims are entitled.

What is claimed is:

1. A method comprising:
    demodulating a data signal incoming to an IMD;
    serially storing demodulated data received in the data signal in a first serial buffer register;
    transferring the received demodulated data to a parallel buffer register from the first serial buffer register, wherein the parallel buffer register operates according to a clock signal having a lower frequency than a clock signal used to operate a serial buffer register;
    switching the serial storing of demodulated data to a second serial buffer register during the transferring of the received demodulated data to the parallel buffer register; and
    alternating the serial storing of the received data between the first and second serial buffer registers.

2. The method of claim 1, including:
    transferring data from the parallel buffer register to the first serial buffer register;
    serially sending data to a modulator from the first serial buffer register; and
    alternating between transferring data from the parallel buffer register to the second serial buffer register during the serial sending of data by the first serial buffer register and transferring data from the parallel buffer register to the first serial buffer register during the sending of data by the second serial buffer register.

3. The method of claim 2, wherein serially sending data to a modulator includes encoding the data, wherein the encoding limits the number of same-value bits in a bit string message.

4. The method of claim 2, wherein serially sending data to a modulator includes serially sending data to a radio frequency modulator.

5. The method of claim 1, including:
    sampling the received data signal a specified number of times during a specified bit time to obtain a specified number of samples of a bit value; and
    determining the bit value according to a majority rule applied to the specified number of samples.

6. The method of claim 5, wherein sampling the received data signal includes sampling the received data signal an odd number of times from a data signal edge detected by a transceiver of the IMD.

7. The method of claim 1, including activating circuits in the IMD when a boundary character is received into the first serial buffer register.

8. The method of claim 7, wherein activating circuits in the IMD includes activating the circuits when the boundary character includes a comma character.

9. The method of claim 7, including declaring a communication message boundary in the IMD when the boundary character is subsequently received into at least one of the first and second serial buffer registers.

10. The method of claim 9, including using at least a portion of the boundary character to adjust an attenuation threshold in a transceiver circuit of the IMD.

11. The method of claim 10, including initiating adjustment of the attenuation threshold when detecting, by the IMD, a first portion of the boundary character and adjusting the attenuation threshold during reception of the remaining portion of the boundary character.

12. The method of claim 1, including:
 encoding, by an external device, data to be transmitted to the IMD; and
 transmitting encoded data serially to the IMD in a bit string, wherein the encoding limits a number of same-value bits in the bit string.

13. The method of claim 12, wherein encoding includes encoding data using 8b/10b encoding.

14. The method of claim 13, wherein transmitting encoded data serially to the IMD includes transmitting encoded data serially to the IMD using an IMD programmer.

15. The method of claim 13, wherein transmitting encoded data serially to the IMD includes first transmitting the encoded data serially to a device remote from both the external device and the IMD.

16. The method of claim 1, including operating the parallel buffer register with a clock signal having a frequency that is approximately thirty-two kilohertz and operating a serial buffer register with a clock signal having a frequency of approximately two megahertz.

17. The method of claim 1, including operating the first and second serial buffer registers with a clock signal having a frequency that is approximately twenty times greater than a clock signal used to operate the parallel buffer register.

18. The method of claim 1, wherein demodulating a data signal incoming to an IMD includes demodulating a data signal received using a far-field antenna.

19. The method of claim 1, wherein demodulating a data signal incoming to an IMD includes demodulating a data signal incoming to at least one of a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device.

20. The method of claim 1, including operating byte level logic using a clock signal frequency used to operate the parallel buffer register.

* * * * *